United States Patent [19]

Browne

[11] Patent Number: 4,536,505
[45] Date of Patent: Aug. 20, 1985

[54] CERTAIN N-(PYRIDYL) INDOLES

[75] Inventor: Leslie J. Browne, Morris Plains, N.J.

[73] Assignee: Ciba-Geigy Corporation, Ardsley, N.Y.

[21] Appl. No.: 495,370

[22] Filed: May 17, 1983

[51] Int. Cl.³ .................... A61K 31/44; C07D 401/04
[52] U.S. Cl. .................... 514/339; 514/333; 514/338; 546/270; 546/273; 546/256
[58] Field of Search .................. 546/273, 256, 270; 424/263

[56] References Cited

U.S. PATENT DOCUMENTS

| | | | |
|---|---|---|---|
| 3,449,348 | 6/1969 | Shen et al. | 424/266 |
| 3,933,853 | 1/1976 | Demarne | 424/274 |
| 4,322,533 | 3/1982 | Lesher et al. | 546/273 |
| 4,363,912 | 12/1982 | Cross et al. | 546/273 |
| 4,416,895 | 11/1983 | Thorogood | 424/273 R |
| 4,451,472 | 5/1984 | Cross et al. | 546/273 |
| 4,460,777 | 7/1984 | Renfroe | 424/263 |
| 4,478,842 | 10/1984 | Renfroe | 546/270 |
| 4,511,573 | 4/1985 | Renfroe | 424/263 |

FOREIGN PATENT DOCUMENTS

| | | | |
|---|---|---|---|
| 299938 | 7/1972 | Austria . | |
| 323154 | 9/1974 | Austria . . | |
| 2171937 | 9/1973 | France . | |
| 2102795 | 2/1983 | United Kingdom | 546/273 |

OTHER PUBLICATIONS

Chemical Abstracts 80, 3381n (1974); Abstract of German Offenlegungsschrift 2,307,708.
Chemical Abstracts 80, 59863p (1974); Abstract of French Demande 2,171,937.
J. Chem. Soc. (C) 1970 p. 85.

Primary Examiner—Jane T. Fan
Attorney, Agent, or Firm—Norbert Gruenfeld

[57] ABSTRACT

Disclosed are compounds of formula I

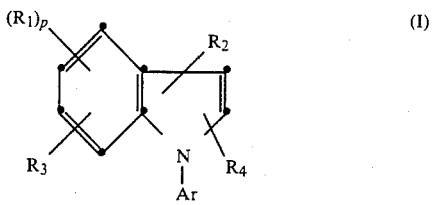

wherein Ar is 3- or 4-pyridyl or 3- or 4-pyridyl substituted by lower alkyl;

$R_1$ is hydrogen, halogen, trifluoromethyl, lower alkyl, hydroxy, acylated or etherified hydroxy, lower alkyl-(thio, sulfinyl or sulfonyl), or two of $R_1$ on adjacent carbon atoms represent alkylenedioxy;

p is 1 or 2;

$R_2$ represents hydrogen or lower alkyl; one of $R_3$ and $R_4$ represents hydrogen and the other of $R_3$ and $R_4$ represents the group A-B in which A represents alkylene of 1 to 12 carbon atoms, alkynylene or alkenylene of 2 to 12 carbon atoms each, lower alkylene-phenylene, lower alkylene-(thio or oxy)-lower alkylene, lower alkylene-(thio or oxy)-phenylene, lower alkylenephenylene-lower (alkylene or alkenylene), or alkadienylene or 4 to 12 carbon atoms; and B represents carboxy, esterified carboxy, carbamoyl, mono- or di-lower alkylcarbamoyl, cyano, hydroxycarbamoyl, or 5-tetrazolyl; the pyridyl-N-oxides thereof; and pharmaceutically acceptable salts thereof; methods for their synthesis and pharmaceutical compositions thereof. These compounds are useful as selective thromboxane synthetase inhibitors for the treatment of diseases such as cerebral ischaemia, shock, thrombosis and ischaemic heart disease.

17 Claims, No Drawings

CERTAIN N-(PYRIDYL) INDOLES

SUMMARY OF THE INVENTION

The present invention is concerned with N-pyridylindoles which are useful as surprisingly potent and highly specific thromboxane synthetase inhibitors.

The foregoing attributes render the N-pyridylindoles of this invention particularly useful when administered, alone or in combination, to mammals, e.g. for the treatment or prevention of diseases responsive to the inhibition of thromboxane synthetase, comprising cardiovascular disorders such as peripheral vascular diseases and Raynaud's syndrome, thrombosis, atherosclerosis, coronary spasm, arrhythmias, cerebral ischaemic attacks, migraine and other vascular headaches, myocardial infarction, angina pectoris, hypertension; respiratory disorders, such as asthma and apnea; and inflammatory disorders.

This invention relates to the N-pyridylindoles of formula I which are useful as selective thromboxane synthetase inhibitors, processes for preparing same, pharmaceutical compositions comprising said compounds, and methods of treating syndromes, conditions and diseases in mammals responsive to the inhibition of thromboxane synthetase by administration of said compounds and compositions.

DETAILED DESCRIPTION OF THE INVENTION

Particularly the invention relates to the N-pyridylindoles of formula I

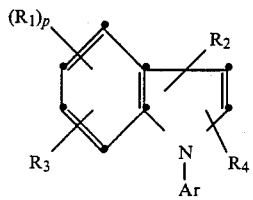

wherein Ar is 3- or 4-pyridyl or 3- or 4-pyridyl substituted by lower alkyl;

$R_1$ is hydrogen, halogen, trifluoromethyl, lower alkyl, hydroxy, acylated or etherified hydroxy, lower alkyl-(thio, sulfinyl or sulfonyl), or two of $R_1$ on adjacent carbon atoms represent alkylenedioxy;

p is 1 or 2;

$R_2$ represents hydrogen or lower alkyl; one of $R_3$ and $R_4$ represents hydrogen and the other of $R_3$ and $R_4$ represents the group A–B in which A represents alkylene of 1 to 12 carbon atoms, alkynylene or alkenylene of 2 to 12 carbon atoms each, lower alkylenephenylene, lower alkylene-(thio or oxy)-lower alkylene, lower alkylene-(thio or oxy)-phenylene, lower alkylenephenylene-lower (alkylene or alkenylene), or alkadienylene of 4 to 12 carbon atoms; and B represents carboxy, esterified carboxy, carbamoyl, mono- or di-lower alkylcarbamoyl, cyano, hydroxycarbamoyl, or 5-tetrazolyl; the pyridyl-N-oxides thereof; and pharmaceutically acceptable salts thereof.

Preferred embodiments of this invention relate to compounds of formula I wherein Ar is 3-pyridyl; $R_1$ is hydrogen, halogen, trifluoromethyl, lower alkyl, lower alkoxy, lower alkylthio, hydroxy or lower alkanoyloxy; p is 1; $R_2$ represents hydrogen or lower alkyl; $R_3$ represents hydrogen; and $R_4$ represents the group A–B in which A has meaning as defined above and B represents carboxy, lower alkoxycarbonyl, carbamoyl, cyano, hydroxycarbamoyl, or 5-tetrazolyl; and pharmaceutically acceptable salts thereof.

Further preferred are said compounds of formula I wherein p is 1, $R_1$ is attached at the 5-position of the indole nucleus; $R_2$ is hydrogen or lower alkyl; $R_3$ is hydrogen; and $R_4$ is the group A–B located at the 3-position of the indole nucleus.

Further preferred are also said compounds of formula I wherein B represents carboxy, lower alkoxycarbonyl, carbamoyl, 5-tetrazolyl or hydroxycarbamoyl.

Greatly preferred are the above-cited compounds of formula I wherein $R_4$ is the group A–B in which A represents alkylene or alkenylene of 3 to 10 carbon atoms each, lower alkylenephenylene of 7 to 10 carbon atoms, lower alkylene-thio-phenylene of 7 to 10 carbon atoms or lower alkylene-oxy-phenylene of 7 to 10 carbon atoms; and B represents carboxy or lower alkoxycarbonyl; $R_1$ represents hydrogen, lower alkyl, halogen, trifluoromethyl, hydroxy, lower alkylthio or lower alkoxy; p is 1; Ar is 3-pyridyl; $R_2$ represents hydrogen or lower alkyl; $R_3$ represents hydrogen; and pharmaceutically acceptable salts thereof.

Most preferred are the compounds of formula I wherein A represents alkylene of 3 to 8 carbon atoms.

A particularly preferred embodiment of the invention is represented by compounds of formula II

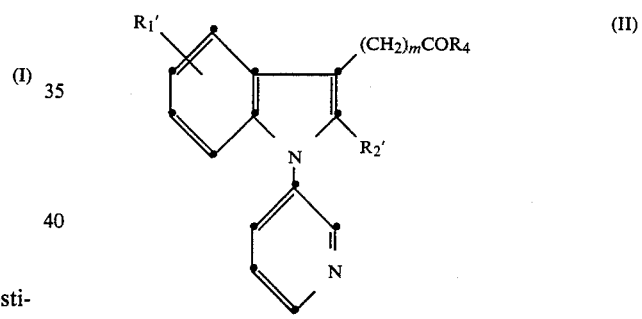

wherein $R_1'$ represents hydrogen, lower alkyl, halogen, trifluoromethyl, hydroxy, lower alkylthio or lower alkoxy;

$R_2'$ represents hydrogen or lower alkyl;

m represents an integer from 1 to 10; $R_4$ represents hydroxy, lower alkoxy or amino; and pharmaceutically acceptable salts thereof.

Further preferred are compounds of formula II wherein $R_1'$ represents hydrogen, methyl, chloro, fluoro, trifluoromethyl, hydroxy, methylthio or methoxy; $R_2'$ represents hydrogen; m represents an integer from 3 to 8; $R_4$ represents hydroxy, ethoxy, methoxy or amino; and pharmaceutically acceptable salts thereof.

Especially preferred are the compounds of formula II above wherein $R_1'$ represents hydrogen or halogen; and pharmaceutically acceptable salts thereof.

Most preferred are the compounds of formula II wherein $R_1'$ represents hydrogen or chloro; $R_2'$ represents hydrogen; m is 4 or 5; $R_4$ represents hydroxy; and pharmaceutically acceptable salts thereof.

Another preferred embodiment of the invention is represented by the compounds of formula III

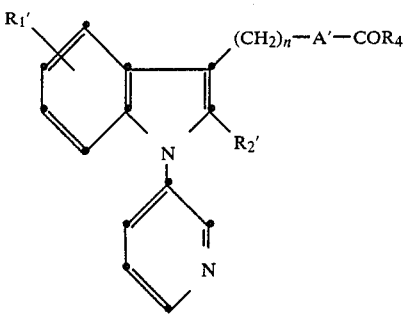

(III)

wherein $R_1'$ represents hydrogen, lower alkyl, halogen, trifluoromethyl, hydroxy, lower alkylthio or lower alkoxy; $R_2'$ represents hydrogen or lower alkyl; $R_4$ represents hydroxy, lower alkoxy or amino; n represents an integer from 1 to 4; A' represents (thio or oxy)-alkylene of 1 to 4 carbon atoms, (thio or oxy)-1,4-phenylene, 1,4-phenylene, ethenylene or lower alkyl-substituted ethenylene; and pharmaceutically acceptable salts thereof.

Preferred in turn are the compounds of formula III wherein A' is ethenylene or lower alkyl-substituted ethenylene; n represents the integer 2 or 3; and pharmaceutically acceptable salts thereof.

The general definitions used herein have the following meanings within the scope of the present invention.

The term "alkylene" represents straight chain or branched alkylene of 1 to 12 carbon atoms, preferably propylene, butylene, pentylene, hexylene, or heptylene, said radicals being unsubstituted or substituted by one or more lower alkyl groups with the proviso that the total number of carbon atoms equals no more than 12.

The term "alkenylene" represents straight chain or branched alkenylene of 2 to 12 carbon atoms, preferably propenylene, 1- or 2-butenylene, 1- or 2-pentenylene, 1-, 2- or 3-hexenylene, 1-, 2-, 3- or 4-heptenylene, said groups being unsubstituted or substituted by one or more lower alkyl groups with the proviso that the total number of carbon atoms equals no more than 12.

The term "alkynylene" represents straight chain or branched alkynylene of 2 to 12 carbon atoms, preferably propynylene, 1- or 2-butynylene, 1- or 2-pentynylene, 1-, 2- or 3-hexynylene, 1-, 2-, 3- or 4-heptynylene, said radicals being unsubstituted or substituted by one or more lower alkyl groups with the proviso that the total number of carbon atoms equals no more than 12.

The term "alkadienylene" represents straight chain or branched conjugated or unconjugated alkadienylene of 4 to 12 carbon atoms, e.g. butadienylene, 1,3- or 1,4-pentadienylene, 1,3-, 1,4-, or 1,5-hexadienylene, 1,3-, 1,4-, 1,5- or 1,6-heptadienylene said radicals being unsubstituted or substituted by one or more lower alkyl groups with the proviso that the total number of carbon atoms equals no more than 12.

The term phenylene represents 1,2-, 1,3- and preferably 1,4-phenylene.

The term "lower" when referred to above and hereinafter in connection with organic groups, radicals or compounds respectively defines such with up to and including 7, preferably up to and including 4 and advantageously one, two or three carbon atoms.

A lower alkylenephenylene group, a lower alkylenephenylene-lower (alkylene or alkenylene) group, a lower alkylene-(thio or oxy)-phenylene group, preferably contains 1 to 4 carbon atoms and advantageously one or two carbon atoms in each alkylene, or 2 to 4 carbon atoms in each alkenylene portion. The lower alkylene and alkenylene portions may be straight chain or branched.

A lower alkylene-(thio or oxy)-lower alkylene group is straight chain or branched and may contain a total of 2 to 12 carbon atoms, preferably 2 to 8 carbon atoms.

A lower alkyl group preferably contains 1–4 carbon atoms and represents for example ethyl, propyl, butyl or advantageously methyl.

A lower alkylene group preferably contains 1–4 carbon atoms and represents for example methylene, ethylene, 1,2- or 1,3-propylene, 1,2- 1,3- or 1,4-butylene.

A lower alkylenedioxy group represents preferably ethylenedioxy and methylenedioxy.

A lower alkoxy group preferably contains 1–4 carbon atoms and represents for example, ethoxy, propoxy or advantageously methoxy. A lower alkyl-(thio, sulfinyl or sulfonyl) group represents advantageously methylthio, methylsulfinyl or methylsulfonyl respectively.

A lower alkoxycarbonyl group preferably contains 1–4 carbon atoms in the alkoxy portion and represents for example: methoxycarbonyl, propoxycarbonyl, isopropoxycarbonyl or advantageously ethoxycarbonyl. A mono(lower alkyl)-carbamoyl group preferably contains 1–4 carbon atoms in the alkyl portion and is for example N-methylcarbamoyl, N-propylcarbamoyl, or advantageously N-ethylcarbamoyl. A di(lower alkyl)-carbamoyl group preferably contains 1–4 carbon atoms in each lower alkyl portion and represents for example N,N-dimethylcarbamoyl, N-methyl-N-ethylcarbamoyl and advantageously N,N-diethylcarbamoyl.

Halogen is preferably fluorine and chlorine, but may also represent bromine or iodine.

An aryl group, such as in aryl-lower alkoxy represents preferably phenyl, phenyl mono- or di-substituted by lower alkyl, halogen or lower alkoxy, or pyridyl.

An aryl-lower alkoxy group advantageously represents benzyloxy.

Acylated hydroxy represents preferably lower alkanoyloxy e.g. acetyloxy, benzoyloxy, benzoyloxy substituted on the phenyl ring by lower alkyl, halogen or lower alkoxy, e.g. methyl, chloro or methoxy respectively, or nicotinoyloxy.

Etherified hydroxy represents preferably lower alkoxy, e.g. methoxy, benzyloxy, benzyloxy substituted on the phenyl ring by lower alkyl, halogen or lower alkoxy, e.g. methyl, chloro or methoxy respectively, or pyridylmethoxy.

Esterified carboxy represents preferably carboxy esterified preferably as a pharmaceutically acceptable ester, advantageously an ester that may be convertible by solvolysis or under physiological conditions to the free carboxylic acid, e.g. lower alkoxycarbonyl; (amino, mono- or di-lower alkylamino)-substituted lower alkoxycarbonyl; carboxy-substituted lower alkoxycarbonyl, e.g. α-carboxy-substituted lower alkoxycarbonyl; lower alkoxycarbonyl-substituted lower alkoxycarbonyl, e.g. α-lower alkoxycarbonyl-substituted lower alkoxycarbonyl; aryl-substituted lower alkoxycarbonyl, e.g. optionally substituted benzyloxycarbonyl or pyridylmethoxycarbonyl; (hydroxy, lower alkanoyloxy or lower alkoxy)-substituted lower alkoxycarbonyl, e.g. pivaloyloxymethoxycarbonyl; (hydroxy, lower alkanoyloxy or lower alkoxy)-substituted lower alkoxymethoxycarbonyl; bicycloalkoxycarbonyl-substituted lower alkoxycarbonyl, e.g. bicyclo[2,2,1]-heptyloxycarbonyl-substituted lower alkoxycarbonyl, especially bicyclo[2,2,1]heptyloxycarbonyl-substituted methoxy such as bornyloxycarbonylmethoxycarbonyl; 3-phthalidoxycarbonyl; (lower alkyl, lower alkoxy, halo)-substituted 3-phthalidoxycarbonyl, lower alkoxycarbonyloxy-lower alkoxycarbonyl, e.g. 1-(methoxy or ethoxycarbonyloxy)-ethoxycarbonyl; aryloxycarbonyl, e.g. phenoxycarbonyl or phenoxycarbonyl advantageously substituted at the ortho position by carboxy or lower alkoxycarbonyl.

Pharmaceutically acceptable salts are preferably metal or ammonium salts of said compounds of formula I having a free carboxy group, more particularly alkali or alkaline earth metal salts, e.g., the sodium, potassium, magnesium or calcium salt; or advantageously easily crystallizing ammonium salts derived from ammonia or organic amines, such as mono- di- or tri-lower (alkyl, cycloalkyl or hydroxyalkyl)-amines, lower alkylenediamines or lower (hydroxyalkyl or aralkyl)-alkylammonium hydroxides, e.g., methylamine, diethylamine, triethylamine, dicyclohexylamine, triethanolamine, ethylenediamine, tris-(hydroxymethyl)aminomethane or benzyltrimethylammonium hydroxide. Said compounds of Formula I form acid addition salts of preferably the pharmaceutically acceptable inorganic or organic acids, such as of strong mineral acids, for example hydrohalic, e.g. hydrochloric or hydrobromic acid; sulfuric, phosphoric, nitric or perchloric acid; aliphatic or aromatic carboxylic or sulfonic acids, e.g. formic, acetic, propionic, succinic, glycolic, lactic, malic, tartaric, gluconic, citric, ascorbic, maleic, fumaric, pyruvic, phenylacetic, benzoic, 4-aminobenzoic, anthranilic, 4-hydroxybenzoic, salicylic, 4-aminosalicylic, pamoic, nicotinic, methanesulfonic, ethanesulfonic, hydroxyethanesulfonic, benzenesulfonic, p-toluenesulfonic, naphthalenesulfonic, sulfanilic or cyclohexylsulfamic acid.

The compounds of this invention exhibit valuable pharmacological properties, e.g. cardiovascular effects, by selectively decreasing thromboxane levels through selective inhibition of thromboxane synthetase in mammals. The compounds are thus useful for treating diseases responsive to thromboxane synthetase inhibition in mammals, primarily cardiovascular disorders such as thrombosis, atherosclerosis, coronary spasm, cerebral ischaemic attacks, migraine and other vascular headaches, myocardial infarction, angina pectoris, and hypertension.

These effects are demonstrable in in vitro tests or in vivo animal tests using advantageously mammals, e.g. guinea pigs, mice, rats, cats, dogs, or monkeys, Said compounds can be administered to them enterally or parenterally, advantageously orally, or subcutaneously, intravenously or intraperitoneally, for example, within gelatin capsules, or in the form of starchy suspensions or aqueous solutions respectively. The applied dosage may range between about 0.01 to 100 mg/kg/day, preferably between about 0.05 and 50 mg/kg/day, advantageously between about 0.1 and 25 mg/kg/day.

The in vitro inhibition of the thromboxane synthetase enzyme can be demonstrated, analogous to the method of Sun, Biochem. Biophys. Res. Comm. 74, 1432 (1977); the testing procedure is as follows: $^{14}$C-Arachidonic acid is incubated with an enzyme consisting of solubilized and partially purified prostaglandin cyclo-oxygenase from sheep seminal vesicles and a crude microsomal preparation of thromboxane synthetase from lysed human platelets. The test compound (dissolved in buffer, or if necessary, in a small amount of ethanol) is added to the incubation medium. At the end of the incubation period (30 minutes), Prostaglandin E$_2$ (PGE$_2$) is reduced to a mixture of Prostaglandin F$_{2\alpha}$ and F$_2\beta$ (PGF$_{2\alpha}$+$\beta$) by addition of sodium borohydride. The radioactive products and excess substrate are extracted into ethyl acetate; the extract is evaporated to dryness; the residue is dissolved in acetone, spotted on thin-layer plates and chromatographed in the solvent system toluene:acetone:glacial acetic acid (100 volumes:100 volumes:3 volumes). The radioactive zones are located; those corresponding to Thromboxane B$_2$ (T×B$_2$) and PGF$_{2\alpha}$+$\beta$ are transferred to liquid scintillation vials and counted. The ratio of counts for T×B$_2$/PGF$_{2\alpha}$+$\beta$ is calculated for each concentration of test compound and IC$_{50}$ values are determined graphically as the concentration of test compound at which the ratio of T×B$_2$/PGF$_{2\alpha}$+$\beta$ is reduced to 50% of the control value.

The in-vitro effect on prostaglandin cyclooxygenase is measured by a modification of the method of Takeguchi et al. described in Biochemistry 10, 2372 (1971); the testing procedure is as follows:

Lyophilized sheep seminal vesicle microsomes are utilized as the prostaglandin-synthesizing enzyme preparation. The conversion of $^{14}$C-arachidonic acid to PGE$_2$ is measured. Test compounds (dissolved in buffer, or if necessary, in a small amount of ethanol) are added to the incubation mixture. The prostaglandins are extracted and separated by thin-layer chromatography; the plates are scanned, the radioactive zones corresponding to PGE$_2$ are transferred to liquid scintillation vials and counted for radioactivity. IC$_{50}$ values for inhibition are determined graphically as the concentration of test compound causing a 50% reduction in the amount of PGE$_2$ synthesized.

The in-vitro effect on prostacyclin (PGI$_2$) synthetase is measured analogous to the method of Sun et al., Prostaglandins 14, 1055 (1977);

The testing procedure is as follows: $^{14}$C-Arachidonic acid is incubated with an enzyme mixture consisting of solubilized and partially purified prostaglandin cyclooxygenase from sheep seminal vesicles and crude PGI$_2$ synthetase in the form of a microsomal fraction of bovine aorta.

Test compound (dissolved in buffer, or if necessary, in a small amount of ethanol) is placed in the incubation medium. The reaction mixture is incubated in 100 mM Tris HCl (pH 7.5) for 30 minutes at 37° C., acidified to pH 3 and extracted into ethyl acetate. The extract is evaporated to dryness; the residue is dissolved in acetone, spotted on thin-layer plates and chromatographed in a solvent system described by Sun et al. The radioactive zones are located with a scanner; those corresponding to 6-keto-PGF$_{1\alpha}$ (a stable end product of prostacyclin biotransformation) and PGE$_2$ are transferred to liquid scintillation vials and counted. The ratio of counts for 6-keto-PGF$_{1\alpha}$/PGE$_2$ is calculated for each concentration of test compound used. IC$_{50}$ values for inhibition are determined graphically as the concentration of test compound at which the ratio of 6-keto-PGF$_{1\alpha}$/PGE$_2$ is reduced to 50% of the control value.

The inhibition of the synthesis and the reduction of plasma levels of thromboxane is determined in vivo on administration to rats in the following manner (as adapted from the procedures described by Tai et al. in Anal. Biochem. 87:343, 1978 and by Salmon in Prostaglandins 15:383, 1978):

Rats are dosed with vehicle or test drug and injected intravenously with ionophore A23187 (0.5 mg/kg) two hours later. Blood is collected for analysis 2 minutes after the ionophore injection. A single aliquot of each plasma sample is assayed for thromboxane $B_2$ and another aliquot for 6-keto-PGF$_{1\alpha}$, the stable metabolites of thromboxane $A_2$ and prostacyclin (PGI$_2$) respectively, by radioimmunoassay.

Compounds of the formula I are very potent and selective thromboxane synthetase inhibitors. At the effective dose levels for thromboxane synthetase inhibition neither the beneficial prostacyclin synthetase enzyme system nor the prostaglandin cyclooxygenase enzyme system is significantly inhibited. The prostacyclin levels are actually significantly increased.

Illustrative of the invention, the IC$_{50}$ for 3-(4-carboxybutyl)-N-(3-pyridyl)indole is about $1.1 \times 10^{-9}$M for thromboxane synthetase inhibition. The IC$_{50}$ for cyclooxygenase inhibition is greater than $1 \times 10^{-3}$M.

Further illustrative of the invention the IC$_{50}$ for thromboxane synthetase inhibition is e.g. about $4.0 \times 10^{-9}$M for 3-(5-carboxypentyl)-N-(3-pyridyl)indole, and about $2.6 \times 10^{-9}$M for 3-(4-carboxybutyl)-5-chloro-N-(3-pyridyl)indole.

3-(4-Carboxybutyl)-N-(3-pyridyl)indole, as a representative illustrative compound of the invention, decreases the plasma concentration of thromboxane $B_2$ by over 50% in the rat at an oral dose of 0.04 mg/kg or lower; an approximately 5-fold increase in the plasma level of prostacyclin is observed.

The aforementioned advantageous properties render the compounds of this invention of great value as specific therapeutic agents for mammals including man.

Indicative of the utility in thromboembolism, compounds of this invention also prolong bleeding time in the rat. Illustrative of a beneficial antithrombotic effect, 3-(4-carboxybutyl)-N-(3-pyridyl)indole prolongs bleeding time when administered orally to rats at a dose of about 1.0 mg/kg p.o.

Compounds of the invention also demonstrate lipoxygenase inhibition indicative of anti-inflammatory activity. Lipoxygenase inhibition is determined as follows:

Guinea pig peritoneal neutrophils (elicited by an i.p. injection of sodium caseinate 17 hours prior to harvesting) are preincubated with indomethacin (1 μM) and test drugs for 5 minutes at 37° C. $^{14}$C-arachidonic acid (4 μM) and calcium ionophore A-23187 (2 μM) are added and the samples are incubated for another 5 minutes at 37° C. The reaction is terminated by the addition of 1N HCl and the products are extracted with ethyl acetate and separated by thin-layer chromatography; the plates are scanned and the radioactive zones corresponding to LTB$_4$ and 5-HETE are scraped off, transferred to liquid scintillation vials and counted for radioactivity.

Illustrative of the invention, the IC$_{50}$ for 5-chloro-3-(4-carboxybutyl)-N-(3-pyridyl)indole in lipoxygenase inhibition is about $3 \times 10^{-5}$M.

In addition to the pharmaceutically acceptable salts cited above, any prodrug derivatives thereof, e.g., pharmaceutically acceptable esters and amides of the carboxylic acids of this invention that may be convertible by solvolysis or under physiological conditions to the said carboxylic acids, represent a further object of this invention.

Said prodrug esters are preferably e.g., the straight chain or branched lower alkyl esters unsubstituted or suitably substituted such as the pivaloyloxymethyl, 2-diethylaminoethyl, bornyloxycarbonylmethyl, α-carboxyethyl or suitably esterified α-carboxyethyl esters and the like which are prepared by methods well known to the art.

Said prodrug amides are preferably e.g. simple primary and secondary amides and amides derived from the amino acids or derivatives thereof, such as the amides derived from alanine, phenylalanine and the like.

The compounds of formula I according to the invention can be prepared by processes comprising, e.g.

(1) condensing a compound of the formula IV

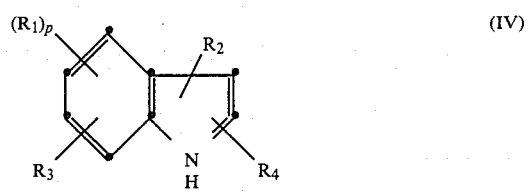

wherein $R_1$–$R_4$ and p have meaning as defined hereinabove with a compound of the formula ArX wherein Ar has meaning as previously defined and X represents reactive esterified hydroxy;

(2) condensing a compound of the formula V,

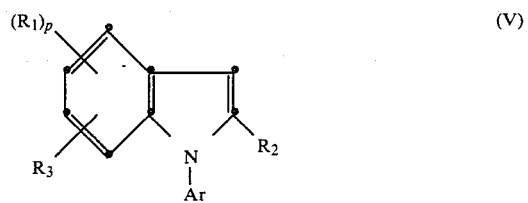

or a 3halo derivative thereof, wherein $R_1$, p and $R_2$ have meaning as previously defined, and $R_3$ represents hydrogen, with a reactive functional derivative of a compound of the formula VI

HO—A—B (VI)

wherein A and B have meaning as defined above, with optional temporary protection of interfering reactive groups;

(3) ring-closing a compound of formula VII

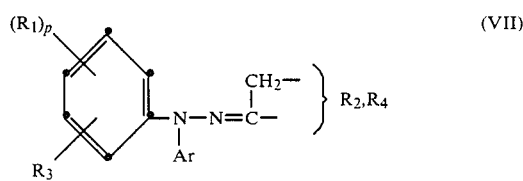

containing one $R_2$ and one $R_4$, and wherein $R_1$–$R_4$, p and Ar have meaning as previously defined;

(4) cyclizing a compound of the formula VIII

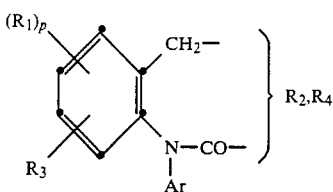

(VIII)

containing one $R_2$ and one $R_4$, and wherein $R_1$–$R_4$, and Ar have meaning as defined above; or (5) cyclizing a compound of the formula IX

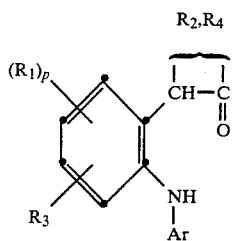

(IX)

containing one $R_2$ and $R_4$, and wherein $R_1$–$R_4$, p and Ar have meaning as defined above;

(6) converting into a compound of formula I a compound of the formula Ia

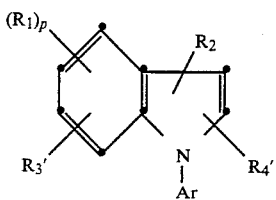

(Ia)

wherein Ar, $R_1$, p and $R_2$ have meaning as defined above, one of $R_3'$ and $R_4'$ represents hydrogen and the other of $R_3'$ and $R_4'$ represents the group A–C in which C is a group differing from B and convertible into B; and/or if desired, converting a resulting compound of formula I obtained by any of the above processes into another compound of formula I, and/or if desired, converting a resulting compound of formula I obtained by any of the above processes into a salt thereof, or liberating a free compound from such salt; and/or if appropriate, isolating an optical or geometric isomer which is enriched from a mixture of isomeric forms of a resulting compound of formula I.

Compounds of formula I also may be prepared by (7) condensing a compound of the formula

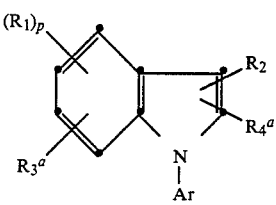

(X)

wherein Ar, $R_1$, p and $R_2$ have meaning as previously defined, one of $R_3{}^a$ and $R_4{}^a$ represents hydrogen and the other of $R_3{}^a$ and $R_4{}^a$ represents formyl or lower alkanoyl; with a compound of the formula

$R_5$—A''—B       (XI)

wherein A'' represents A as previously defined but in which the chain length is shortened by 1 carbon atom; $R_5$ represents a dialkylphosphono or a triarylphosphonium radical; and, if appropriate, reducing the double bond which is directly attached to the indole ring in the resulting product.

(8) condensing a compound of the formula XII

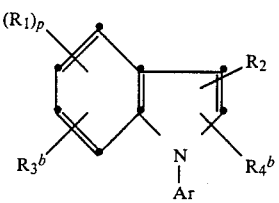

(XII)

wherein Ar, $R_1$, p and $R_2$ have meaning as previously defined, one of $R_3{}^b$ and $R_4{}^b$ represents hydrogen and the other of $R_3{}^b$ and $R_4{}^b$ represents reactive esterified hydroxy, e.g. halo, with a compound of the formula XIII

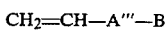

$CH_2=CH-A'''-B$       (XIII)

wherein A''' represents A as previously defined in which the chain length is shortened by 2 carbon atoms or A''' represents a direct bond; and when appropriate reducing the double bond which is directly attached to the indole ring in the resulting product.

For the condensation according to process (1) a compound of formula IV is condensed with a compound ArX, X being preferably bromo, advantageously in the presence of an Ullmann reaction [see Organic Reactions 14, 19 (1965)] catalyst, e.g. copper, copper bronze, copper oxide, triphenylphosphine-nickel, preferably in a polar solvent such as pyridine, dimethylformamide, optionally in the presence of an anhydrous base such as potassium carbonate, at a temperature between about 75° C. and 150° C., e.g. about 100° C., or as generally described in J. Chem. Soc. (C), 1970 pages 85–91.

The starting indoles of formula IV are either known or if new are prepared by methods well-known in the art, e.g. the Fischer indole synthesis or as described in the examples herein.

For the condensation according to process (2), the compounds of formula V or 3-halo derivatives thereof, are first converted to reactive organometallic derivatives, e.g., the alkali metal or halomagnesium (Grignard) derivatives with an appropriate metallizing agent e.g. a Grignard reagent, an alkali metal base or a quaternary ammonium base. More specifically, compounds of formula V are converted preferably in situ, to reactive organometallic intermediates with a reactive metallizing agent, preferably about one molar equivalent of e.g. a strong alkali metal base, such as butyllithium, lithium diisopropylamide, sodium hydride, potassium t-butoxide, a Grignard reagent e.g. a lower alkyl magnesium halide such as methylmagnesium bromide in an inert solvent such as dimethylformamide, diethyl ether or tetrahydrofuran at a temperature range between −50° to +75° preferably between −25° and +50°. Condensation of the resulting reactive organometallic compound of formula V with a reactive esterified derivative of a compound of formula VI proceeds at a temperature range from about −25° to +50°, preferably at a temperature range of 0° to 30°. In the case where B represents carboxy, carbamoyl, hydroxycarbamoyl, mono lower alkylcarbamoyl, an additional e.g. one molar equivalent of metallizing agent is required.

The intermediates of formula V are either known to the art (e.g. J. Chem. Soc. (C) 1970, 85) or are prepared analogously e.g. from the corresponding optionally substituted indoles, such as described in the examples herein.

The starting materials of formula VI are known or if new, are prepared according to conventional methods, e.g. the methods illustrated in U.S. Pat. No. 4,256,757, British patent application 2,016,452A.

The ring closure according to process (3) of the intermediates of formula VII is carried out by the well-known Fischer indole synthesis [as described e.g. in "Heterocyclic Compounds, Indoles Part I" edited by W. J. Houlihan pp. 232–317] thermally or preferably in the presence of an acid condensing agent, advantageously a hydrogen halide, e.g. ethanolic hydrogen chloride, or polyphosphoric acid, optionally in an inert solvent preferably at a temperature of about 50°–100° C.

The intermediate hydrazones of formula VII are either isolated or are preferably prepared in situ by the condensation of a ketone of the formula $R_2CH_2COR_4$ or $R_4CH_2COR_2$, wherein $R_2$ and $R_4$ have the meaning as previously described for the compounds of formula I, with a hydrazine of the formula XIV

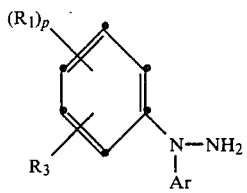

(XIV)

wherein the symbols $R_1$, p, Ar and $R_3$ have meaning as previously defined for the compounds of formula I, advantageously in the presence of an acid catalyst.

The starting hydrazines of formula XIV are known or are in turn preferably prepared by e.g. nitrosation of the correspondingly substituted anilines of formula XV

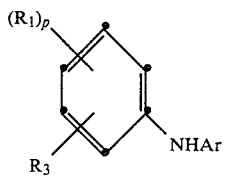

(XV)

wherein the symbols $R_1$, p, Ar and $R_3$ have meaning as previously defined, and subsequent reduction of the N-nitroso derivatives, e.g. with zinc in acetic acid or by other methods well-known to the art.

If any intermediates mentioned herein contain interfering reactive groups, e.g. carboxy, hydroxy or amino groups, such may advantageously be temporarily protected at any stage with easily removable blocking groups, e.g. in the form of esters or amides by methods well known to the art.

The cyclization according to process (4) is carried out under conditions of the Madelung indole synthesis as described in "Heterocyclic Compounds, Indoles Part I", edited by W. J. Houlihan, pp. 385–396. The intramolecular cyclization is preferably carried out in the presence of a strong base, e.g. sodium ethoxide, sodium amide, potassium t-butoxide advantageously at elevated temperature e.g. ca. 300° neat or in an inert high boiling solvent such as tetrahydronaphthalene.

The intermediates of formula VIII are prepared by acylation of the substituted anilines of formula XVI and XVIA

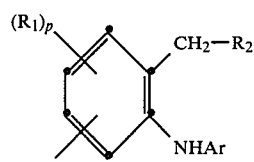

(XVI)

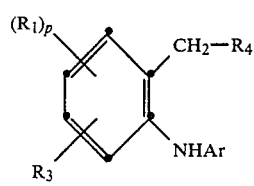

(XVIA)

wherein $R_1$–$R_4$, p and Ar have meaning as previously defined, with a compound of the formula $R_4COOH$ and $R_2COOH$ respectively or a reactive functional derivative thereof wherein $R_2$ and $R_4$ have meaning as previously defined.

The cyclization according to process (5) maybe carried out in the presence of a strong base, e.g. potassium t-butoxide, or sodium hydride in a polar solvent such as dimethylformamide, or dimethoxyethane.

The conversion of a compound of formula Ia according to a process (6) wherein C differs from B into a compound of formula I, and the optional conversion of resulting product of formula I into another compound of this invention are performed by chemical methodology known to the art, and/or e.g. as described herein.

A convertible group C preferably represents trialkoxymethyl, hydroxymethyl, esterified hydroxymethyl, etherified hydroxymethyl, halomethyl, 2-oxazolinyl, dihydro-2-oxazolinyl, lower alkanoyloxymethyl, acetyl, methyl, carboxycarbonyl, formyl, trihaloacetyl, di(lower)alkoxymethyl, alkylenedioxymethyl, vinyl, alkynyl, esterified carboxy, amidated carboxy.

The intermediates of formula Ia are prepared according to the processes described herein, using conventional chemical methodology well known to the art.

The intermediates of formula Ia are also active as thromboxane synthetase inhibitors.

The condensation according to process (7) is carried out under conditions used in the art for a Wittig type condensation, e.g. as described in J. Am. Chem. Soc. 83, 1733 (1961) under ylid forming conditions, e.g. in the presence of a strong base such as sodium hydride, in a solvent such as methylene chloride, toluene at a temperature ranging from −20° to +100°, preferably from −10° to +50°.

The condensation according to process (8) is carried out e.g. as generally described in Accounts of Chemical Research 12, 146 (1979) in the presence of e.g. a triarylphosphine, e.g. tri-o-tolylphosphine, and a palladium salt, e.g. palladium acetate, and a base, e.g. triethylamine, in a polar solvent, e.g. said base or acetonitrile, at a temperature preferably ranging from about 25° to 100°

C. to give initially a product of the invention wherein the group $R_3$ or $R_4$ contains a double bond directly attached to the indole ring.

The starting materials of formula XII, e.g. wherein one of $R_3^b$ and $R_4^b$ represents bromo are prepared by conventional methods well-known in the art, e.g. as described in Can. J. Chemistry 41, 2399 (1963).

Certain terms used in the foregoing processes have the meaning as defined below.

Reactive esterified hydroxy, such as in reactive functional derivatives of alcohols of formula VI, represents e.g. hydroxy esterified by a strong inorganic or organic acid above all a hydrohalic acid, e.g. hydrochloric, hydrobromic or hydriodic acid, an aliphatic or aromatic sulfonic acid, e.g. methanesulfonic acid, p-toluenesulfonic acid, prepared by methods known in the art.

Trialkoxymethyl represents preferably tri(lower alkoxy)-methyl, particularly triethoxy- or trimethoxymethyl.

Etherified hydroxymethyl represents preferably tertiary lower alkyloxymethyl, lower alkoxyalkoxymethyl such as methoxymethyloxymethyl, 2-oxa- or 2-thiacycloalkoxymethyl particularly 2-tetrahydropyranyloxymethyl.

Esterified hydroxymethyl represents preferably lower alkanoyloxymethyl, advantageously acetoxymethyl.

Halomethyl represents especially chloromethyl but may also be bromomethyl or iodomethyl.

An alkali metal represents preferably lithium but may also be potassium or sodium.

The conversion of the compounds of formula Ia to compounds of formula I and the interconversions of the compounds of this invention are carried out by chemical methodology well-known to the art.

Compounds of formula I and intermediates wherein $R_1$ is aryl-lower alkoxy, e.g. benzyloxy, or lower alkoxy, e.g. methoxy, can be converted to compounds wherein $R_1$ is hydroxy by hydrogenolysis or hydrolysis respectively, using methods well known in the art.

The compounds of formula I wherein B represents hydroxycarbamoyl (hydroxamic acids) may be prepared by condensing a compound of formula I, wherein B represents carboxy or a reactive functional derivative thereof, lower alkoxycarbonyl or carbamoyl, with hydroxylamine or an acid addition salt thereof in the presence of a basic reagent, e.g. sodium hydroxide. Said condensation is carried out according to methods per se e.g. as described in Barton et al., Comprehensive Organic Chemistry, Vol. 2 pp. 1037–1038 (1979), preferably under basic conditions advantageously with hydroxylamine hydrochloride, in an inert polar solvent, e.g. a lower alkanol such as ethanol, preferably at a temperature range of about 0° to 50°, advantageously at room temperature.

The compounds of formula I wherein B represents 5-tetrazolyl may be prepared by condensing a compound of formula I, wherein B represents preferably cyano, with hydrazoic acid or a compound which serves as a source of hydrazoic acid, e.g. a metal or ammonium salt of hydrazoic acid, preferably an alkali metal azide such as sodium azide or ammonium azide. Said condensation is carried out according to methods known per se, e.g. as described in Barton et al, Comprehensive Organic Chemistry Vol. 4. pp. 407–409 (1979), preferably in a solvent such as dimethylformamide and at an elevated temperature ranging from about 50° to 200°, advantageously 75° to 150°, and in the presence of an acid, e.g. hydrochloric acid or ammonium chloride.

Said tetrazoles may also be prepared from a compound of formula I wherein the group C representing cyano or carbamoyl is first converted to a (halo or lower alkoxy)-iminocarbonyl group for condensation with e.g. an alkali metal azide or ammonium azide.

The compounds of formula Ia wherein C represents 4,5-dihydro-2-oxazolyl are preferably prepared by condensing a compound of formula I, wherein C represents carboxy or a reactive functional derivative thereof, lower alkoxycarbonyl or carbamoyl, with 2-hydroxyethylamine or with aziridine.

The condensation is carried out according to methods generally known per se, e.g. as described in J. Organic Chemistry 39, 2787 (1974), preferably in an inert solvent such as toluene at a temperature range of about 25°–100°. Said condensation occurs either spontaneously or in the presence of condensing agents, e.g. disubstituted carbodiimides, such as dicyclohexylcarbodiimide, in the case where C represents carboxy.

Intermediates of formula Ia wherein C is halomethyl may be reacted preferably with a metal cyanide such as potassium cyanide in a conventional manner to yield the compounds of formula I wherein the chain is extended by 1 carbon atom and B is cyano. These in turn are converted to compounds of formula I wherein B is carboxy, alkoxycarbonyl or carbamoyl using methods known to the art.

Thus, the compounds of formula I wherein B represents cyano (nitriles) are converted to compounds of formula I wherein B is carboxy by hydrolysis with inorganic acids e.g. a hydrohalic acid such as hydrochloric acid or sulfuric acid in aqueous solution, or advantageously by hydrolysis with aqueous alkali metal hydroxide e.g. potassium hydroxide at reflux temperature.

The conversion of said nitriles to compounds of formula I wherein B represents lower alkoxycarbonyl is advantageously carried out by treatment first with a lower alkanol, e.g. anhydrous ethanol, in the presence of a strong acid, e.g. hydrochloric acid preferably at reflux temperature, followed by careful hydrolysis with water.

Furthermore, the conversion of the said nitriles to compounds of formula I wherein B represents carbamoyl is preferably carried out by treatment with an alkali metal hydroxide, e.g. dilute sodium hydroxide, and hydrogen peroxide, preferably at room temperature.

Furthermore, the intermediates of formula Ia wherein C is halomethyl, such as chloromethyl, are converted to compounds of formula I, wherein B is carboxy and the chain length is extended by two carbons, by first treating with e.g. a di-(lower)alkyl malonate, such as diethyl malonate, in the presence of a base such as potassium carbonate or sodium ethoxide, in a solvent such as dimethylformamide, preferably at a temperature range from 50° to 100°. The resulting substituted di(lower)alkyl malonate is hydrolyzed, advantageously with aqueous base, such as dilute sodium hydroxide, to the corresponding malonic acid which is decarboxylated under standard conditions, e.g. by heating in xylene solution, to give a compound of formula I wherein B is carboxy. Substitution of the di-(lower)alkyl malonate with a lower alkyl cyanoacetate yields the corresponding compounds of formula I wherein B is cyano.

Compounds of the invention, wherein A represent straight chain or branched alkenylene with a terminal double bond, may also be prepared from intermediates for formula Ia wherein C is halomethyl. For instance, said intermediates are first treated with e.g. a lower alkyl ester of an α-(aryl- or alkyl)thioacetic acid such as ethyl α-(phenylthio)-acetate, in the presence of a strong base such as sodium hydride. Subsequent oxidation of the resulting α-arylthio or α-alkylthio substituted ester to the α-arylsulfinyl or α-alkylsulfinyl ester with e.g. sodium periodate, followed by heat-induced elimination, by e.g. refluxing in xylene, yields a compound of general formula I (an α,β-unsaturated ester) wherein A represents alkenylene and B represents e.g. lower alkoxycarbonyl, and the chain length has been extended by two carbon atoms. The same transformation is also carried out using e.g. ethyl α-(phenylselenno)acetate as described in J. Am. Chem. Soc. 95, 6137(1973). Similarly, the compounds of formula Ia wherein C represents halomethyl may first be converted to the corresponding carboxaldehydes with e.g. dimethylsulfoxide in the presence of triethylamine and silver tetrafluoroborate, or with chromium trioxide and pyridine in methylene chloride. Subsequent Wittig condensation e.g. with trimethylphosphonoacetate or ethyl(triphenylphosphoranylidene)acetate also yields the above-cited α,β-unsaturated esters.

Compounds of formula I wherein B is lower alkoxycarbonyl may be amidized with ammonia, mono- or di-(lower)alkylamines e.g. methylamine, dimethylamine in an inert solvent, e.g. a lower alkanol, such as butanol, optionally at elevated temperatures to yield compounds of formula I wherein B represents unsubstituted, mono- or di(lower)alkylcarbamoyl.

Compounds of formula I wherein A contains straight chain or branched alkylene with a terminal double bond, e.g. α,β-unsaturated esters, may also be prepared from the corresponding α,β-saturated compounds by treatment with e.g. phenylselenyl chloride in the presence of a strong base according to the procedure described in J. Am. Chem. Soc. 95, 6137 (1973).

Conversion of compounds of formula I wherein B is lower alkoxycarbonyl; cyano; unsubstituted, mono- or di-(loweralkyl)carbamoyl to compounds of formula I wherein B represents carboxy is advantageously carried out by hydrolysis with inorganic acids such as hydrohalic or sulfuric acid or with aqueous alkalies, preferably alkali metal hydroxides such as lithium or sodium hydroxide.

Compounds of formula I wherein B represents carboxy or lower alkoxycarbonyl may be reduced with simple or complex light metal hydrides such as lithium aluminum hydride, alane or diborane to compounds of formula Ia wherein B is hydroxymethyl. Said alcohols are also obtained by appropriate solvolysis of compounds of formula Ia wherein C is halomethyl by treatment with e.g. in alkali metal hydroxide such as lithium or sodium hydroxide.

Said alcohols may in turn be transformed to the compounds of formula I wherein B is carboxy with conventional oxidizing agents, advantageously with pyridinum dichromate in dimethylformamide at room temperature.

Free carboxylic acids may be esterified with lower alkanols such as ethanol in the presence of a strong acid, e.g. sulfuric acid, advantageously at elevated temperature or with diazo(lower)alkanes, e.g. diazomethane in a solvent such as ethyl ether, advantageously at room temperature, to give the corresponding esters, namely compounds of formula I wherein B is lower alkoxycarbonyl.

Furthermore, the free carboxylic acids may be converted via treatment of a reactive intermediate thereof, e.g. an acyl halide such as the acid chloride, or a mixed anhydride, e.g. such derived from a lower alkyl halocarbonate such as ethyl chloroformate, with ammonia, mono- or di-(lower)alkylamines, in an inert solvent such as methylene chloride, preferably in the presence of a basic catalyst such as pyridine, to compounds of formula I wherein B represents unsubstituted, mono or di-(lower)alkylcarbamoyl.

Compounds of formula I wherein B represents mono(lower)alkylcarbamoyl are converted to compounds of formula I wherein B is di-(lower)alkyl-carbamoyl by treatment of the former with a strong base e.g. sodium hydride followed by an alkylating agent, e.g. a lower alkyl halide in an inert solvent, e.g. dimethylformamide.

Furthermore compounds of formula Ia wherein A represents a straight chain or branched alkynylene or alkenylene may be converted by catalytic hydrogenation, advantageously under neutral conditions e.g. with palladium catalyst at atmospheric pressure in an inert solvent, e.g. ethanol, to compounds of formula I wherein A represents straight chain or branched alkylene.

The carboxaldehydes, the compounds of formula I wherein B represents formyl, may be prepared by oxidizing compounds of formula Ia wherein C represents respectively hydroxymethyl or halomethyl with e.g. dimethyl sulfoxide and a catalyst, such as a mixture of triethylamine and silver tetrafluoroborate, or with chromium trioxide and pyridine or other oxidizing agents known in the art. Said carboxaldehydes are converted to the corresponding acetals, the compounds of formula Ia wherein C represents di(lower)alkoxymethyl, or alkylenedioxymethyl e.g. a dimethylacetal, by acid-catalyzed condensation with an alcohol, e.g. methanol.

Compounds of formula I wherein B represents carboxy may be converted by the well-known Arndt-Eistert synthesis to compounds of formula I wherein B represents carboxy and the chain has been extended by 1 carbon atom. More particularly, a reactive functional derivative of the starting carboxylic acid, e.g. the acid chloride, is treated with diazomethane in e.g. diethyl ether to yield a compound of formula Ia wherein C represents diazoacetyl. Rearrangement with e.g. silver oxide yields said carboxylic acid of formula I wherein the chain has been extended by 1 carbon atom.

A specific embodiment of process (5) is for the preparation of compounds of formula I wherein B represents carboxy and comprises converting in a compound of the formula Ia in which C represents a functionally modified carboxyl group, the group C into carboxy, optionally by extending the chain A within its definition.

Groups convertible into a carboxy group are, for example, esterified carboxy groups, carboxy groups in form of their anhydrides, including corresponding groups of asymmetrical and inner anhydrides, amidated carboxy groups, cyano, amidino groups, including cyclic amidino group such as 5-tetrazolyl, iminoether groups, including cyclic iminoether groups, e.g., 2-oxazolinyl or dihydro-2-oxazolinyl groups substituted by lower alkyl, and also methyl, hydroxymethyl, etherified hydroxymethyl, lower alkanoyloxymethyl, trialkoxymethyl, acetyl, trihaloacetyl, halomethyl, carboxycarbonyl (COCOOH), formyl (CHO), di(lower)alkoxymethyl, alkylenedioxymethyl, vinyl, ethynyl or diazoacetyl. Simultaneously with conversion of C into the carboxy group, the chain A can be extended within its definition.

Esterified carboxy groups are preferably carboxy groups in form of the lower alkyl esters, e.g. the methyl, ethyl, n- or i-(propyl or butyl)esters; substituted lower alkyl esters e.g. the ω-amino, ω-mono- or dimethylamino, α-carboxy or α-carbethoxy(ethyl, propyl or butyl)esters; aryl(lower)alkyl esters, e.g. benzyl, (methyl-, methoxy-, chloro-) substituted benzyl, and pyridylmethyl esters; lower alkanoyloxy-(lower)alkyl esters, e.g. pivaloyloxymethyl esters; 3-phthalidyl and (methyl-, methoxy-, chloro-) substituted 3-phthalidyl esters, derived from the corresponding 3-hydroxyphthalides, (hydroxy-, lower alkanoyloxy-, lower alkoxy-) substituted lower alkoxymethyl esters e.g. β-(hydroxy-, acetyloxy-, methoxy-)ethoxymethyl esters; bicycloalkyloxy-carbonyl-(lower)alkyl esters, e.g. those derived from bicyclic monoterpenoid alcohols, such as unsubstituted or lower alkyl substituted bicyclo[2,2-1]heptyloxycarbonyl-(lower)alkyl esters, advantageously bornyloxycarbonylmethyl esters; halo substituted lower alkyl esters, e.g. trichloroethyl or iodoethyl esters.

Amidated carboxy groups are preferably carboxy groups in form of their unsubstituted amides; N-mono or di-lower alkylamides, e.g. mono- or di-methylamides; tertiary amides derived from e.g. pyrrolidine, piperidine or morpholine; α-(lower)carboalkoxy- or carboxy-substituted lower alkylamides, e.g. mono N-(carboethoxymethyl)-amides, and mono N-(carboxymethyl)amides; α-(lower)carboalkoxy or carboxy-substituted aryl(-lower)alkylamides, e.g. (carboethoxy or carboxy) substituted phenethylamides; amino(lower)-alkylamides, e.g. β-aminoethylamides and β-(carbobenzyloxyamino)ethylamides.

The conversion into the carboxy group is accomplished by methods which are known per se, and as described herein and in the examples, e.g., by solvolysis such as hydrolysis or acidolysis as previously described, or by reduction (esterified carboxy groups). For example, a trichloroethyl or 2-iodoethyl ester may be converted into the carboxylic acid by reduction, e.g. with zinc and a carboxylic acid in the presence of water. Benzyl esters or nitrobenzyl esters may be converted into the carboxy group by catalytic hydrogenation, the latter also with chemical reducing agents, e.g., sodium dithionite or with zinc and a carboxylic acid. In addition, tert-butyl esters may also be cleaved with the trifluoroacetic acid. During the reduction of the group C, an alkenylene or alkynylene chain A may be converted into the corresponding alkylene chain.

Furthermore, compounds of formula Ia wherein C represents acetyl may be oxidatively cleaved to the corresponding compounds of formula I wherein B represents carboxy by conversion first to a compound of formula Ia wherein C represents trihaloacetyl, e.g. tribromo or triiodoacetyl, by treatment e.g. with sodium hypobromite followed by cleavage with e.g. an aqueous base, such as sodium hydroxide.

The starting materials of formula Ia wherein C represents acetyl are in turn prepared from compounds of formula Ia wherein C represents halomethyl by treatment with an alkyl ester of acetoacetic acid, e.g. ethyl acetoacetate, in the presence of a base, e.g. sodium hydride, followed by hydrolysis with a strong base, e.g., e.g. aqueous sodium hydroxide.

Said compounds are also prepared by condensing a compound of formula Ia wherein C is cyano with e.g. a Grignard or other organometallic reagent, e.g. methyl magnesium bromide under standard conditions.

Compounds of formula Ia wherein C represents carboxycarbonyl (COCOOH) are converted thermally or by oxidation to compounds of formula I wherein C represents carboxy by heating at elevated temperature e.g., at about 200 degrees, in the presence of glass powder, or by treating e.g., with hydrogen peroxide in the presence of a basic agent, e.g. sodium hydroxide.

The starting materials of formula Ia wherein C represents COCOOH are prepared by e.g. condensation of a compound of formula Ia wherein C represents halomethyl with e.g. 2-ethoxycarbonyl-1,3-dithiane, and subsequent oxidative hydrolysis, e.g. with N-bromosuccinimide in aqueous acetone followed by treatment with dilute aqueous sodium hydroxide.

Compounds of formula Ia wherein C represents formyl, di(lower)alkoxymethyl or alkylenedioxymethyl (formyl protected in the form of an acetal), e.g. the dimethyl acetal, are oxidized with e.g. silver nitrate, pyridinium dichromate or ozone to the corresponding compound of formula I wherein B represents carboxy.

Compounds of formula Ia wherein C represents vinyl may be converted to compounds of formula I wherein B represents carboxy by first ozonolysis to compounds of formula I wherein B represents formyl, which are in turn oxidized to compounds of formula I wherein B represents carboxy.

Compounds of formula Ia wherein C represents vinyl may also be treated with nickel carbonyl and carbon monoxide under high pressure conditions to give compounds of formula I wherein B represents carboxy and the chain A contains a double bond adjacent to the carboxyl group.

Compounds of formula Ia wherein C represents ethynyl may be treated with a strong base, e.g. butyl lithium followed by condensation with carbon dioxide or condensation with a lower alkyl haloformate, e.g. ethyl chloroformate followed by hydrolysis to give compounds of formula I wherein B represents carboxy and the chain A contains a triple bond adjacent to the carboxyl group.

Compounds of formula Ia wherein C represents halomethyl may be converted to a corresponding organometallic intermediate, e.g. a cuprous or magnesium derivative, under conditions well known to the art.

Condensation of e.g. the resulting organomagnesium (Grignard) reagent, e.g. a compound of formula Ia wherein C is transformed to e.g. $CH_2MgCl$, with carbon dioxide yields a compound of formula I wherein B represents carboxy and the chain has been extended by 1 carbon atom.

Condensation of said Grignard reagent with e.g. a lower alkyl haloacetate or e.g. ethyl bromoacetate and subsequent hydrolysis yields a compound of formula I wherein B represents carboxy and wherein the chain has been extended by 2 carbon atoms.

Said Grignard reagent may be condensed in the presence of a cuprous halide, e.g. cuprous chloride, with an α,β-unsaturated acid, e.g. propiolic or acrylic acid to yield a compound of formula I wherein B represents carboxy and wherein the chain has been extended by 3 carbon atoms.

Furthermore, compounds of formula Ia wherein C represents halomethyl may be condensed with e.g. the 3-lithio derivative of propiolic acid (prepared with e.g. lithium diisopropylamide) to yield a compound of formula I wherein A contains a terminal alkynylene, B represents carboxy and the chain length has been extended by 3 carbon atoms.

Compounds of formula Ia wherein A represents lower alkylene and C represents hydroxymethyl, as reactive functional derivatives thereof, may be condensed with a lower alkanol (or thiol), or a phenol (or thiophenol) appropriately substituted by B, preferably in the presence of a strong base, to give compounds of formula I wherein A represents lower alkylene-(thio or oxy)-phenylene, or lower alkylene-(thio or oxy)-lower alkylene.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures preferably at the boiling point of the solvents used, and at atmospheric or super-atmospheric pressure. The preferred solvents, catalysts and reaction conditions are set forth in the appended illustrative examples.

The invention further includes any variant of the present processes, in which an intermediate product obtainable at any stage thereof is used as starting material and the remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds indicated above as being especially useful.

The invention also relates to novel starting materials and processes for their manufacture.

Depending on the choice of starting materials and methods, the new compounds may be in the form of one of the possible isomers or mixtures thereof, for example, depending on the presence of a double bond and the number of asymmetrical carbon atoms, as pure optical isomers, such as antipodes, or as mixtures of optical isomers such as racemates, mixtures of diastereoisomers, mixtures of racemates or mixtures of geometrical isomers. The aforesaid possible isomers or mixtures thereof are within the purview of this invention; certain particular isomers may be preferred.

Any resulting mixtures of diastereoisomers, mixtures of racemates and geometric isomers can be separated on the basis of the physicochemical differences of the constituents, in known manner, into the pure isomers, diastereoisomrs, racemates, or geometric isomers, for example by chromatography and/or fractional crystallisation.

Any resulting racemates can be resolved into the optical antipodes by known methods, for example by e.g. reacting an acidic end product with an optically active base that forms salts with the racemic acid, and separating the salts obtained in this manner, for example by fractional crystallization, into the diastereoisomeric salts from which the optically active carboxylic acid antipodes can be liberated on acidification. The basic racemic products can likewise be resolved into the optical antipodes, e.g. by separation of the diastereoisomeric salts thereof, with an optically active acid, and liberating the optically active basic compound by treatment with a standard base. Racemic products of the invention can thus be resolved into their optical antipodes, e.g., by the fractional crystallization of d- or l-(tartrates, mandelates, camphorsulfonates), or of d- or l-($\alpha$-methylbenzylamine, cinchonidine, cinchonine, quinine, quinidine, ephedrine, dehydrobietylamine, brucine or strychnine) salts. Advantageously, the more active of the two antipodes is isolated.

Finally the compounds of the invention are either obtained in the free form, or as a salt thereof. Any resulting base can be converted into a corresponding acid addition salt, preferably with the use of a therapeutically useful acid or anion exchange preparation, or resulting salts can be converted into the corresponding free bases, for example, with the use of a stronger base, such as a metal or ammonium hydroxide or a basic salt, e.g. an alkali metal hydroxide or carbonate, or a cation exchange preparation. A compound of formula I wherein B represents carboxy can thus also be converted into the corresponding metal or ammonium salts. These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The pharmaceutical compositions according to the invention are those suitable for enteral, such as oral or rectal, and parenteral administration to mammals, including man, for the treatment of prevention of diseases responsive to inhibition of thromboxane synthetase, comprising an effective amount of a pharmacologically active compound of formula I, or a pharmaceutically acceptable salt thereof, alone or in combination with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with (a) diluents, e.g. lactose, dextrose, sucrose, mannitol, sorbitol, cellulose and/or glycine; (b) lubricants, e.g. silica, talcum, stearic acid, its magnesium or calcium salt and/or polyethyleneglycol; for tablets also (c) binders, e.g. magnesium aluminum silicate, starch paste, gelatin, tragacanth, methylcellulose, sodium carboxymethylcellulose and/or polyvinylpyrrolidone; if desired (d) disintegrants, e.g. starches, agar, alginic acid or its sodium salt, or effervescent mixtures; and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient. A unit dosage for a mammal of about 50 to 70 kg may contain between about 10 to 100 mg of the active ingredient.

The following examples are intended to illustrate the invention and are not to be construed as being limitations thereon. Temperatures are given in degrees Centigrade, and all parts wherever given are parts by weight. If not mentioned otherwise, all evaporations are performed under reduced pressure, preferably between about 15 and 100 mmHg.

EXAMPLE 1

A solution of 1.27 ml of diisopropylamine in 25 ml of tetrahydrofuran is cooled to −65° under nitrogen and 5.7 ml of 1.6M n-butyllithium in hexane is added. After 30 minutes at −65°, 2.0 ml of triethyl 4-phosphonocrotonate is added dropwise. The reaction mixture is stirred for 30 minutes before a solution of 2.0 g of N-(3-pyridyl)indole-3-carboxaldehyde in 20 ml of tetrahydrofuran is slowly added while maintaining the temperature less than −60°. When the addition is complete, cooling is suspended and the reaction mixture slowly warms to room temperature at which temperature it is stirred for 4 hours. The solvent is evaporated and the residue is partitioned between 30 ml of methylene chloride and 20 ml of half saturated ammonium chloride solution. The organic phase is washed with 20 ml of water, dried over sodium sulfate and evaporated to give an oil which crystallizes from hot ethyl acetate to yield 3-[4-(ethoxycarbonyl)butadienyl]-N-(3-pyridyl)-indole, m.p. 112°–113°.

The starting materials are prepared as follows:

A solution of 2.12 ml of N,N-dimethylformamide in 20 ml of 1,2-dichloroethane is cooled to 0° and 3.1 ml of phosphorus oxychloride is added dropwise. The reaction is stirred for 10 minutes at 15° and recooled to 0° before a solution of 4.85 g of N-(3-pyridyl)indole in 10 ml of 1,2-dichloroethane is added. After 2 hours at 5°, the reaction mixture is refluxed for 15 minutes, cooled to room temperature and a solution of 18.75 g of sodium acetate trihydrate in 25 ml of water is added. After an additional 15 minutes at reflux, the organic phase is separated, washed with sodium bicarbonate and water, and dried over magnesium sulfate. Filtration, evaporation and recrystallization of the residue from methylene chloride-methanol yields N-(3-pyridyl)-indole-3-carboxaldehyde, m.p. 148°–150°.

N-(3-Pyridyl)indole is prepared according to J. Chem. Soc. (C) 85 (1970).

EXAMPLE 2

A solution of 6.0 g of 3-[(4-ethoxycarbonyl)-butadienyl]-N-(3-pyridyl)-indole in 60 ml of 95% ethanol is hydrogenated at 3 atmospheres pressure with 0.6 g of 10% palladium on charcoal until the theoretical amount of hydrogen is consumed. The solution is filtered through celite and evaporated to yield 3-[4-(ethoxycarbonyl)butyl]-N-(3-pyridyl)indole; IR (Nujol) 1720 cm$^{-1}$.

EXAMPLE 3

A mixture of 6.8 g of 3-[(4-ethoxycarbonyl)butyl]-N-(3-pyridyl)indole and 1.68 of sodium hydroxide in 30 ml of water and 30 ml of methanol is refluxed for 30 minutes, stirred for 4 hours, at room temperature and concentrated to a syrup, which is redissolved in 30 ml of water at 5°. The solution is neutralized with 3.5 ml of concentrated hydrochloric acid. The resulting ol crystallizes, is filtered off and dried to yield 3-(4-carboxybutyl)-N-(3-pyridyl)-indole, m.p. 122°–124°.

EXAMPLE 4

A solution of 8.0 g of ethyl 3-(3-indolyl)propionate and 6.3 g of 3-bromopyridine in 100 ml of pyridine is refluxed with 5.0 g of copper oxide and 10 g of anhydrous potassium carbonate for 48 hours. Evaporation and chromatography on 300 g of silica with 1:1 ethyl ether:hexane as eluant yields 3-[2-(ethoxycarbonyl)ethyl]-N-(3-pyridyl)indole as an oil; $R_f$=0.2, IR (CH$_2$Cl$_2$) 1725 cm$^{-1}$.

The starting material is prepared as follows:

A solution of 7.38 g of 3-indolepropionic acid and 5.9 g of thionyl chloride in 50 ml of ethanol is refluxed for 2 hours, cooled and evaporated. The residue is partitioned between ether and cold sodium bicarbonate solution. The organic phase is separated, dried over sodium sulfate and evaporated to yield ethyl 3-(3-indolyl)propionate; $R_f$(ether/SiO$_2$)=0.51; IR (CH$_2$Cl$_2$) 1725 cm$^{-1}$.

EXAMPLE 5

A solution of 2.0 g of 3-[2-(ethoxycarbonyl)ethyl]-N-(3-pyridyl)indole in 10 ml of methanol and 10 ml of 1N sodium hydroxide is refluxed for two hours, cooled, and evaporated. The residue is taken up in 10 ml of water, extracted with 10 ml of ether and adjusted to pH=6 with concentrated sulfuric acid. The resulting solid is filtered and dried to yield 3-(2-carboxyethyl)-N-(3-pyridyl)indole, m.p. 147°–149°.

EXAMPLE 6

A solution of 2.7 g of 3-[2-(ethoxycarbonyl)ethyl]-N-(3-pyridyl)indole in 50 ml of dry methylene chloride under nitrogen is cooled to −75° and 10.6 ml of 1.75M diisobutylaluminum hydride in toluene is added dropwise. The reaction is stirred for 8 minutes and quenched with 10 ml of water at −75°. Cooling is stopped and the layers are separated. The organic phase is washed with water, dried over potassium carbonate and evaporated to a solid which is recrystallized from ether-hexane to yield 3-(2-formylethyl)-N-(3-pyridyl)indole, m.p. 44°–45°.

EXAMPLE 7

A solution of lithium diisopropylamide (from 0.53 g of diisopropylamine in 30 ml of tetrahydrofuran and 3.15 ml of 1.65M n-butyllithium) is cooled to −75° under nitrogen and 1.19 g of triethyl 2-phosphonopropionate is added dropwise. The reaction is stirred for 45 minutes and a solution of 0.90 g of 3-(2-formylethyl)-N-(3-pyridyl)indole in 10 ml of tetrahydrofuran is added. The reaction is stirred for 15 minutes at −75°, allowed to warm to room temperature over 45 minutes, quenched with excess ammonium chloride solution and diluted with 30 ml of ethyl ether. The organic phase is separated, dried over potassium carbonate and evaporated to yield a mixture of (E) and (Z)-3-[4-(ethoxycarbonyl)pent-3-enyl]-N-(3-pyridyl)indole as an oil; $R_f$ (SiO$_2$/2:1 ether:hexane)=0.33 and 0.40 respectively.

EXAMPLE 8

A solution of 1.4 g of (Z) and (E)-3-[4-(ethoxycarbonyl)pent-3-enyl]-N-(3-pyridyl)indole in 10 ml of methanol and 6.0 ml of 1N sodium hydroxide is refluxed for 3 hours, cooled and evaporated. The residue is redissolved in 10 ml of water, the solution is adjusted to pH=6 with concentrated sulfuric acid and extracted with chloroform. The organic phase is dried over sodium sulfate and evaporated. The resulting oil is redissolved in acetone and 1.13 ml of 3N ethereal hydrogen chloride is added dropwise. The resulting salt is filtered off to yield (E)-3-(4-carboxypent-3-enyl)-N-(3-pyridyl)indole hydrochloride, m.p. 210°–211°.

The mother liquors are evaporated and the residue is recrystallized from acetone to yield (Z)-3-(4-carboxypent-3-enyl)-N-(3-pyridyl)indole hydrochloride, m.p. 134°–135°.

EXAMPLE 9

A solution of 2.5 g ethyl 3-(3-indolyl)-butyrate and 1.15 ml of 3-bromopyridine in 25 ml of pyridine is refluxed with 1.25 g of copper oxide and 1.25 g of potassium carbonate for 72 hours, filtered and evaporated to a brown oil which is chromatographed on 64 g of silica with 8:1 toluene-ethyl acetate to yield 3-(3-ethoxycarbonyl-2-propyl)-N-(3-pyridyl)indole; $R_f$ (15% EtOAc, 85% toluene/silica gel)=0.35; IR ($CH_2Cl_2$) 1725 $cm^{-1}$.

Ethyl 3-(3-indolyl)-butyrate is prepared according to Chem. Pharm. Bull. 30, 3092 (1982).

EXAMPLE 10

A solution of 2.66 g of 3-(3-ethoxycarbonyl-2-propyl)-N-(3-pyridyl)indole in 15 ml of methanol and 15 ml of water containing 0.7 g of sodium hydroxide is stirred at room temperature for 18 hours, refluxed for 15 minutes, cooled and evaporated. The residue is redissolved in 25 ml of water, neutralized to pH 6 with 1.44 ml of concentrated hydrochloric acid. The resulting oil is extracted into methylene chloride and the extract is dried over sodium sulfate. Filtration and evaporation gives an oil which is redissolved in 5 ml of tetrahydrofuran and treated with 0.55 ml of concentrated hydrochloric acid. The resulting semi-solid is crystallized from methanol-ether to yield 3-(3-carboxy-2-propyl)-N-(3-pyridyl)indole hydrochloride, m.p. 205°–207°.

EXAMPLE 11

A solution of 1.0 g of 3-(2-formylethyl)-N-(3-pyridyl)indole in 15 ml of methylene chloride under nitrogen is cooled to −20° and 4.6 ml of 1.75M diisobutylaluminum hydride in toluene is added dropwise. The reaction is allowed to warm to room temperature for 2 hours and 20 ml of water is added with vigorous stirring. The reaction mixture is filtered through celite which is further washed with methylene chloride. The organic phase is separated, dried over potassium carbonate and evaporated to yield 3-(3-hydroxypropyl)-N-(3-pyridyl)indole as an oil; IR ($CH_2Cl_2$) 3480 $cm^{-1}$.

EXAMPLE 12

A solution of 0.36 g of ethyl mercaptoacetate in 20 ml of dimethylformamide is treated with 0.145 g of a 50% oil dispersion of sodium hydride at room temperature under nitrogen for 15 minutes. A solution of 1.13 g of N-(3-pyridyl)indole-3-propyl benzenesulfonate in 5 ml of dimethylformamide is added at room temperature. The reaction mixture is stirred for 15 hours, diluted with 100 ml of water and extracted 4 times with 50 ml of ethyl ether. The organic extracts are washed with 50 ml of water and 20 ml of cold 1N hydrochloric acid. The acid phase is extracted with ether and brought to pH=8.5 with 50% sodium hydroxide solution. The aqueous phase is extracted with chloroform (3×30 ml). The chloroform extract is dried over potassium carbonate and evaporated to yield 3-[3-(ethoxycarbonylmethylthio)propyl]-N-(3-pyridyl)indole; IR ($CH_2Cl_2$) 1725 $cm^{-1}$.

The starting material is prepared as follows:

A solution of 1.0 g of 3-(3-hydroxypropyl)-N-(3-pyridyl)indole in 40 ml of dry pyridine at 0° is treated with 0.7 g of benzenesulfonyl chloride and stored at 0° for 14 hours. The solvent is evaporated and the residue is partitioned between ethyl ether and aqueous sodium bicarbonate solution. The organic phase is separated, dried over potassium carbonate and evaporated to yield crude N-(3-pyridyl)indole-3-propyl benzenesulfonate as an oil which is used without further purification.

EXAMPLE 13

A solution of 90 mg of 3-[3-(ethoxycarbonylmethylthio)propyl]-N-(3-pyridyl)indole in 5 ml of methanol and 1 ml of 1N sodium hydroxide is refluxed for 10 hours, cooled and evaporated. The resulting oil is partitioned between ether and water. The aqueous phase is brought to pH=6 with concentrated sulfuric acid, is extracted with chloroform and the chloroform extract is dried over sodium sulfate. Filtration and evaporation gives an oil which is redissolved in 2 ml of acetone and is treated with 0.07 ml of 3N ethereal hydrogen chloride. Evaporation and crystallization from acetone-ether yields 3-[3-(carboxymethylthio)propyl]-N-(3-pyridyl)indole hydrochloride, m.p. 106°–110°.

EXAMPLE 14

A solution of dimsyllithium (from 80 ml of dimethylsulfoxide and 13 ml of 2.1M n-butyllithium) is stirred under nitrogen at room temperature, and 6.2 g of 5-carboxypentyltriphenylphosphonium bromide is added in portions. The reaction mixture is stirred for 30 minutes and 3.0 g of N-(3-pyridyl)indole-3-carboxaldehyde is added. After 18 hours at room temperature, the reaction mixture is diluted with 240 ml of water and extracted with 100 ml of ethyl acetate. The aqueous phase is neutralized with 1.1 ml of concentrated hydrochloric acid and extracted with ethyl acetate. The extracts are dried over sodium sulfate and evaporated to an oil which is triturated with ether to give a semi-solid which is recrystallized from methanol to yield 3-(6-carboxyhex-1-enyl)-N-(3-pyridyl)indole, m.p. 124°–125°.

EXAMPLE 15

A solution of 0.5 g of 3-(5-carboxyhex-1-enyl)-N-(3-pyridyl)indole in 25 ml of 95% ethanol is hydrogenated at 3 atmospheres pressure with 0.1 g of 10% palladium on charcoal for 17 hours, filtered through celite and evaporated to an oil. Crystallization from methanol yields 3-(6-carboxyhexyl)-N-(3-pyridyl)indole, m.p. 120°–122°.

EXAMPLE 16

A solution of lithium diisopropylamide (from 1.4 ml of diisopropylamine and 6.3 ml of 1.6M n-butyllithium in hexane) in 25 ml of dry tetrahydrofuran under nitrogen is cooled to −70° and 2.14 ml of triethyl 2-phosphonopropionate is added dropwise. The reaction mixture is stirred for 20 minutes at −70° and 2.0 g of N-(3-pyridyl)indole-3-carboxaldehyde is added. The reaction is allowed to warm to room temperature for 14 hours. The solvent is evaporated and the residue is partitioned between 20 ml of half saturated ammonium chloride solution and 30 ml of methylene chloride. The organic phase is separated, dried over sodium sulfate and evaporated to a solid which is recrystallized from methanol to yield 3-[2-(ethoxycarbonyl)prop-1-enyl]-N-(3-pyridyl)indole, m.p. 97°–99°.

EXAMPLE 17

A solution of 1.1 g of 3-[2-(ethoxycarbonyl)-prop-1-enyl]-N-(3-pyridyl)indole, and 0.288 g of sodium hydroxide in 10 ml of methanol and 10 ml of water is heated under reflux for 2 hours, cooled and evaporated. The resulting oil is redissolved in 10 ml of ice water and is neutralized with 0.59 ml of concentrated hydrochloric acid. The resulting solid is filtered and dried to yield 3-(2carboxyprop-1-enyl)-N-(3-pyridyl)indole, m.p. 213°–215°.

EXAMPLE 18

A solution of lithium diisopropylamide (from 0.57 ml of diisopropylamine and 2.5 ml of 1.6M n-butyllithium in hexane) in 20 ml of dry tetrahydrofuran under nitrogen is cooled to −70° and 0.78 ml of triethyl 4-phosphonocrotonate is added dropwise. The reaction mixture is stirred for 30 minutes at −70°, and then a solution of 0.9 g of N-(3-pyridyl)indole-2-carboxaldehyde in 5 ml of tetrahydrofuran is added slowly. The reaction mixture is allowed to warm to room temperature, is stirred for 14 hours and is evaporated to an oil which is partitioned between 15 ml of half-saturated ammonium chloride solution and 40 ml of ethyl ether. The organic phase is washed with 10 ml of water, dried over sodium sulfate and evaporated to yield 2-[4-(ethoxycarbonyl)-butadienyl]-N-(3-pyridyl)indole as a waxy solid; $R_f$ (10% methanol and toluene, silica gel)=0.7.

The starting material is prepared as follows:

A solution of 10.0 g of 2-carboethoxyindole and 5 ml of 3-bromopyridine in 50 ml of pyridine is refluxed with 5.0 g of copper oxide and 5.0 g of potassium carbonate for 72 hours. Filtration and evaporation yields an oil which is chromatographed on 110 g of silica with 15% ethyl acetate in toluene to yield 2-carboethoxy-N-(3-pyridyl)indole as an oil; IR ($CH_2Cl_2$) 1705 cm$^{-1}$.

A solution of 5.0 g of 2-carboethoxy-N-(3-pyridyl)indole in 75 ml of dry ether is cooled to 5° and 0.7 g of lithium aluminum hydride is added in portions. Cooling is suspended and the reaction mixture is stirred at room temperature under nitrogen for 18 hours and re-cooled to 5°. Sequential addition of 0.7 ml of water, 0.7 ml of 15% sodium hydroxide and 2.1 ml of water produces a fine precipitate which is removed by filtration through celite. The filtrate is dried over sodium sulfate and evaporated to yield crude 2-hydroxymethyl-N-(3-pyridyl)indole which is used without further purification; $R_f$(9:1 toluene:methanol, silica gel)=0.2.

A solution of 3.3 g of 2-hydroxymethyl-N-(3-pyridyl)indole in 33 ml of dry toluene under nitrogen is refluxed with 16.5 g of silver carbonate for 24 hours. Filtration through celite and evaporation yields an oil which is purified by preparative layer chromatography on silica with methylene chloride-ethyl acetate (8:2) as the eluent to yield N-(3-pyridyl)indole-2-carboxaldehyde, m.p. 101°–103° C.

EXAMPLE 19

A solution of 1.1 g of 2-[4-(ethoxycarbonyl)-butadienyl)-N-(3-pyridyl)indole in 25 ml of 95% ethanol is hydrogenated at 3 atmospheres pressure with 0.2 g of 10% palladium on charcoal for 3½ hours. The reaction mixture is filtered through celite and evaporated to yield 2-[4-(ethoxycarbonyl)butyl]-N-(3-pyridyl)indole as a yellow oil; $R_f$(15% ethyl acetate in toluene/silica gel)=0.65; IR ($CH_2Cl_2$) 1726 cm$^{-1}$.

EXAMPLE 20

A solution of 1.0 g of 2-[4-(ethoxycarbonyl)butyl]-N-(3-pyridyl)indole and 0.25 g of sodium hydroxide in 5 ml of methanol and 5 ml of water is stirred for 17 hours at room temperature. The solvent is evaporated and the residue is redissolved in 10 ml of water and neutralized with 0.515 ml of concentrated hydrochloric acid. The resulting product is recrystallized from methanol to yield 2-(4-carboxybutyl)-N-(3-pyridyl)indole, m.p. 143°–144°.

EXAMPLE 21

The following compounds are prepared by methods analogous to those described in the previous examples.

| Compound | Name |
| --- | --- |
| 1 | 3-(3-Carboxypropyl-N—(3-pyridyl)indole, m.p. 134–135°. |
| 2 | 5-Bromo-3-(4-carboxybutyl)-N—(3-pyridyl)indole, m.p. 118–120°. |
| 3 | 3-(4-Carboxybutyl)-2-methyl-N—3-pyridyl)indole, m.p. 112–114°. |
| 4 | 3-(4-Carboxybutyl)-7-methyl-N—(3-pyridyl)indole, m.p. 118–119°. |
| 5 | 3-(4-Carboxybutyl)-5-methoxy-N—(3-pyridyl)indole, m.p. 100°. |
| 6 | 3-(4-Carboxybutyl)-5-chloro-N—(3-pyridyl)indole, m.p. 120–122°. |
| 7 | 3-(4-Carboxybutyl)-5-methyl-N—(3-pyridyl)indole, m.p. 76–77°. |
| 8 | 3-(4-Carboxybutadienyl)-5-methoxy-N—(3-pyridyl) indole, m.p. 215–217°. |
| 9 | 3-(4-ethoxycarbonylbutyl)-5-methoxy-N—(3-pyridyl)-indole hydrochloride, m.p. 108–110°. |
| 10 | 3-(5-carboxypent-1-enyl)-N—(3-pyridyl)indole m.p. 146–8°. |
| 11 | 3-(5-carboxypentyl)-N—(3-pyridyl)indole, m.p. 132–3°. |
| 12 | 3-(6-carboxyhex-2-enyl)-6-chloro-N—(3-pyridyl)-indole hydrochloride monohydrate, m.p. 156–158°. |

Compounds 2–9 and 12 are prepared starting with either 5-bromo-, 2-methyl-, 7-methyl-, 5-methoxy-, 5-chloro-, 5-methyl- or 6-chloro indole respectively which is e.g. first converted to the corresponding N-(3-pyridyl)indole according to J. Chem. Soc. (C), 85 (1970).

Compound 10 is prepared e.g. from N-(3-pyridyl)indole-3-carboxaldehyde and 4-carboxybutyltriphenylphosphonium bromide according to example 14.

Compound 1 is prepared e.g. by treatment of ethyl 3-indolebutyrate with 3-bromopyridine followed by hydrolysis, as described in the previous examples.

EXAMPLE 22

A suspension of 26.6 g of 3-(4-carboxybutyl)-N-(3-pyridyl)indole and 10.5 g of sulfamide in 90 ml of sulfolane is treated with 11.42 g of thionyl chloride at room temperature under nitrogen. The mixture is heated at 120° until gas evolution ceases and solid p-toluenesulfonic acid monohydrate (1.71 g) is added carefully. After heating an additional 3 hours at 120°, the reaction mixture is cooled, poured onto 200 g of ice and acidified with 130 ml of 1N hydrochloric acid. The aqueous phase is sequentially extracted with ethyl acetate (3×100 ml), made basic with solid sodium bicarbonate and reextracted with ethyl acetate (3×125 ml). The organic extracts are washed with 0.5N sodium hydroxide (5×50 ml), dried over sodium sulfate and evaporated to yield and oil which is chromatographed on 60 g of silica gel to yield 3-(4-cyanobutyl)-N-(3-pyridyl)indole.

EXAMPLE 23

A mixture of 5.16 g of 3-(4-cyanobutyl)-N-(3-pyridyl)indole, 1.88 g of sodium azide, 1.57 g of ammonium chloride and 10 mole % of lithium chloride is heated in 14 ml of dry N,N-dimethylformamide at 125° C. for 17 hours. The reaction mixture is cooled, filtered and evaporated to a residual oil which is partitioned between 50 ml of water and 50 ml of ethyl acetate. The aqueous phase is adjusted to pH=2, extracted with 20 ml of ethyl acetate, adjusted to pH=5 and the resulting solid collected by filtration. Treatment with 6.2 ml of 3N ethereal hydrogen chloride yields 3-[4-(5-tetrazolyl)butyl]-N-(3-pyridyl)indole hydrochloride.

EXAMPLE 24

A solution of hydroxylamine (from 2.06 g of hydroxylamine hydrochloride and 2.02 g of sodium hydroxide) and 7.6 g of 3-(4-methoxycarbonylbutyl)-N-(3-pyridyl)indole in 25 ml of methanol is allowed to stand at room temperature for 20 hours. The methanol is evaporated and the residue is taken up in 5 ml of water and adjusted to pH=7. The mixture is extracted with methylene chloride, the extract is washed with water, dried and evaporated to dryness yielding 3-[4-(hydroxycarbamoyl)butyl]-N-(3-pyridyl)indole.

EXAMPLE 25

A solution of 5.0 g of 3-(4-carboxybutyl)-N-(3-pyridyl)indole in 50 ml of methanol is refluxed under nitrogen with 0.25 g of concentrated sulfuric acid for 2 hours. The reaction mixture is cooled and evaporated and partitioned between 50 ml of ether and 50 ml of ice-cold, saturated sodium bicarbonate solution. The organic phase is separated, dried over potassium carbonate and evaporated to yield 3-(4-methoxycarbonylbutyl)-N-(3-pyridyl)indole.

EXAMPLE 26

A solution of 6.1 g of ethanolamine and 2.94 g of 3-(4-carboxybutyl)-N-(3-pyridyl)indole are heated at 170° for 3 hours. Excess ethanolamine is removed by distillation under reduced pressure to yield 3-[4-(4,5-dihydrooxazol-2-yl)butyl]-N-(3-pyridyl)indole.

EXAMPLE 27

A solution of 6.0 g of 3-(4-carboxybutyl)-N-(3-pyridyl)indole in 50 g of thionyl chloride is refluxed for 30 minutes, cooled and 50 ml of toluene is added. The solvents are evaporated and the residue is redissolved in 50 ml of dry methylene chloride at 0°. Gaseous ammonia is bubbled through the solution for 30 minutes. Evaporation of the solvent yields 3-(4-carbamoylbutyl)-N-(3-pyridyl)indole.

Similarly prepared using methylamine and dimethylamine, respectively, are: 3-[4-(N-methylcarbamoyl)butyl]-N-(3-pyridyl)indole and 3-[4-(N,N-dimethylcarbamoyl)butyl]-N-(3-pyridyl)indole.

EXAMPLE 28

A solution of 0.75 g of 5-bromo-N-(3-pyridyl)indole and 0.5 g of ethyl acrylate in 20 ml of triethylamine is refluxed for 48 hours with 10.8 mg of palladium acetate and 30 mg of tri-o-tolylphosphine. The reaction mixture is cooled, evaporated and chromatographed on 20 g of silica gel with diethyl ether to yield 5-(2-ethoxycarbonylethenyl)-N-(3-pyridyl)indole. Saponification by refluxing for 15 hours in 30 ml of ethanol with 5 ml of 2N sodium hydroxide yields a solution which is evaporated to dryness. The residue is partitioned between 20 ml of ether and 10 ml of water. The aqueous phase is separated, brought to pH 5 and the resulting solid is filtered to yield 5-(2-carboxyethenyl)-N-(3-pyridyl)indole which melts with decomposition at 180°.

5-Bromo-N-(3-pyridyl)indole is prepared from 5-bromoindole and 3-bromopyridine using methodology described in the previous examples.

EXAMPLE 29

A solution of 4.55 g of ethyl p-hydroxybenzoate in 50 ml of dry dimethylformamide is treated with 1.31 g of 50% sodium hydride dispersion in mineral oil under nitrogen at 0°, stirred for 30 minutes at 0°, and then at room temperature for 15 minutes. A solution of 7.55 g of 3-(methanesulfonyloxymethyl)-N-(3-pyridyl)indole in 10 ml of dry dimethylformamide is added over 5 minutes and the reaction mixture is warmed at 50° for 18 hours. The reaction mixture is poured onto ice, made acidic with concentrated sulfuric acid and extracted with diethyl ether (4×40 ml). The aqueous phase is adjusted to pH=8 and is extracted with diethyl ether (3×100 ml). The organic extracts are washed with water (4×50 ml) and brine (1×50 ml) and dried over anhydrous sodium sulfate. Evaporation and chromatography on 100 g of silica with diethyl ether as the eluent yields 3-[(p-ethoxycarbonylphenoxy)methyl]-N-(3-pyridyl)indole.

The starting material is prepared as follows:

A solution of 3.3 g of 3-hydroxymethyl-N-(3-pyridyl)indole in 25 ml of pyridine is cooled to +5° and 1.36 ml of methanesulfonyl chloride is added dropwise. After 3 hours the reaction is diluted with 75 ml of ice water and 1.5 g of sodium bicarbonate is added. Extraction with methylene chloride (3×25 ml) and drying of the extracts with sodium sulfate yields 3-(methanesulfonyloxymethyl)-N-(3-pyridyl)indole which is used directly in the next step.

EXAMPLE 30

A solution of crude 3-[(p-ethoxycarbonylphenoxy)methyl]-N-(3-pyridyl)-indole (6.5 g) in 60 ml of ethanol and 60 ml of 1N sodium hydroxide is heated under reflux for 3 hours. The ethanol is distilled off, the aqueous phase is washed with ether, acidified with conc. hydrochloric acid to pH=6, and the resulting solid is filtered off to yield 3-[(p-carboxyphenoxy)-methyl]-N-(3-pyridyl)indole. Treatment with ethanolic hydrogen chloride gives 3-[(p-carboxyphenoxy)methyl]-N-(3-pyridyl)indole hydrochloride.

EXAMPLE 31

Preparation by methods analogous to those described in the previous examples of additional compounds of formula I wherein $R_2$ and $R_3$=H, Ar=3-pyridyl, $R_4$=A–B at position 3 of the indole ring and in which B represents carboxy.

| Compound | $(R_1)_p$ | A |
|---|---|---|
| 1 | 5-Cl | $(CH_2)_5$ |

| Compound | $(R_1)_p$ | A |
|---|---|---|
| 2 | 5-Cl | $CH_2$ |
| 3 | 5-F | $(CH_2)_4$ |
| 4 | 5,6-diCl | $(CH_2)_4$ |
| 5 | 5,6-methylenedioxy | $(CH_2)_5$ |
| 6 | 5-OH | $(CH_2)_4$ |
| 7 | 5-SCH$_3$ | $(CH_2)_3$ |
| 8 | H | $(CH_2)_9$ |
| 9 | H | $-CH_2C\equiv C$ |
| 10 | H | $CH_2CH_2OCH_2$ |
| 11 | H | $p\text{-}(CH_2CH_2S)\text{-}C_6H_4$ |
| 12 | H | $p\text{-}(CH_2CH_2)\text{-}C_6H_4$ |
| 13 | 5-Ome | $CH(CH_3)$ |

EXAMPLE 32

Preparation of 10,000 tablets each containing 10 mg of the active ingredient:

| Formula: | |
|---|---|
| 3-(4-Carboxybutyl)-5-chloro-N—(3-pyridyl)indole | 100.00 g |
| Lactose | 1,157.00 g |
| Corn starch | 75.00 g |
| Polyethylene glycol 6,000 | 75.00 g |
| Talcum powder | 75.00 g |
| Magnesium stearate | 18.00 g |
| Purified water | q.s. |

Procedure:

All the powders are passed through a screen with openings of 0.6 mm. Then the drug substance, lactose, talcum, magnesium stearate and half of the starch are mixed in a suitable mixer. The other half of the starch is suspended in 40 ml of water and the suspension added to the boiling solution of the polyethylene glycol in 150 ml of water. The paste formed is added to these powders which are granulated, if necessary, with an additional amount of water. The granulate is dried overnight at 35°, broken on a screen with 1.2 mm openings and compressed into tablets using concave with 6.4 mm diameter, uppers bisected.

EXAMPLE 33

Preparation of 10,000 capsules each containing 25 mg of the active ingredient:

| Formula: | |
|---|---|
| 3-(4-Carboxybutyl)-N—(3-pyridyl)indole | 250.0 g |
| Lactose | 1,650 g |
| Talcum powder | 100.0 g |

Procedure:

All the powders are passed through a screen with openings of 0.6 mm. Then the drug substance is placed in a suitable mixer and mixed first with the talcum, then with the lactose until homogeneous. No. 3 capsules are filled with 200 mg, using a capsule filling machine.

Similarly prepared are tablets and capsules comprising about 10–100 mg of other compounds of the invention, e.g. any other compound given in the examples herein.

What is claimed is:

1. A compound of the formula

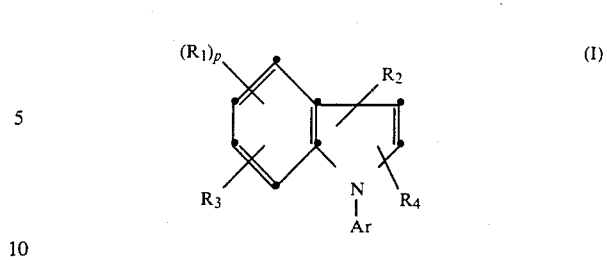

wherein Ar is 3- or 4-pyridyl or 3- or 4-pyridyl substituted by lower alkyl; $R_1$ is hydrogen, halogen, trifluoromethyl, lower alkyl, hydroxy, acylated or etherified hydroxy, lower alkyl-(thio, sulfinyl or sulfonyl), or two of $R_1$ on adjacent carbon atoms represent alkylenedioxy; p is 1 or 2; $R_2$ represents hydrogen or lower alkyl; one of $R_3$ and $R_4$ represents hydrogen and the other of $R_3$ and $R_4$ represents the group A–B in which A represents alkylene of 1 to 12 carbon atoms, alkynylene or alkenylene of 2 to 12 carbon atoms each, lower alkylene-phenylene, lower alkylene-(thio or oxy)-lower alkylene, lower alkylene-(thio or oxy)-phenylene, lower alkylenephenylene-lower (alkylene or alkenylene), or alkadienylene of 4 to 12 carbon atoms; and B represents carboxy, carboxy esterified as a pharmaceutically acceptable ester, carbamoyl, mono- or di-lower alkylcarbamoyl, cyano, hydroxycarbamoyl, or 5-tertrazolyl; a pyridyl-N-oxide thereof; or a pharmaceutically acceptable salt thereof; and wherein within the above definitions acylated hydroxy represents lower alkanoyloxy, benzoyloxy, benzoyloxy substituted on the phenyl ring by lower alkyl, halogen or lower alkoxy, or nicotinoyloxy; etherified hydroxy represents lower alkoxy, benzyloxy, benzyloxy substituted on the phenyl ring by lower alkyl, halogen or lower alkoxy, or pyridylmethoxy.

2. A compound as claimed in claim 1 wherein Ar is 3-pyridyl; $R_1$ is hydrogen, halogen, trifluoromethyl, lower alkyl, lower alkoxy, lower alkylthio, hydroxy or lower alkanoyloxy; p is 1; $R_2$ represents hydrogen or lower alkyl; $R_3$ represents hydrogen; and $R_4$ represents the group A–B in which A has meaning as defined in claim 1 and B represents carboxy, lower alkoxycarbonyl, carbamoyl, cyano, hydroxycarbamoyl, or 5-tetrazolyl; or a pharmaceutically acceptable salt thereof.

3. A compound as claimed in claim 1 wherein p is 1; $R_1$ is attached at the 5-position of the indole nucleus; $R_2$ is hydrogen or lower alkyl; $R_3$ is hydrogen; and $R_4$ is the group A–B located at the 3-position of the indole nucleus; or a pharmaceutically acceptable salt thereof.

4. A compound as claimed in claim 1 wherein $R_4$ is the group A–B in which A represents alkylene or alkenylene of 3 to 10 carbon atoms each, lower alkylenephenylene of 7 to 10 carbon atoms, lower alkylene-thiophenylene of 7 to 10 carbon atoms or lower alkyleneoxy-phenylene of 7 to 10 carbon atoms; and B represents carboxy or lower alkoxycarbonyl; $R_1$ represents hydrogen, lower alkyl, halogen, trifluoromethyl, hydroxy, lower alkylthio or lower alkoxy; p is 1; Ar is 3-pyridyl; $R_2$ represents hydrogen or lower alkyl; $R_3$ represents hydrogen; or a pharmaceutically acceptable salt thereof.

5. A compound of the formula

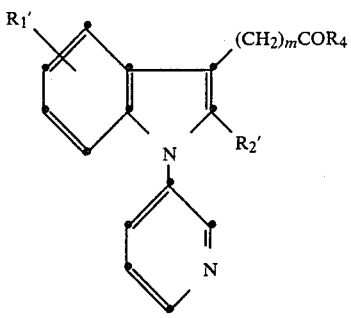

(II)

wherein $R_1'$ represents hydrogen, lower alkyl, halogen, trifluoromethyl, hydroxy, lower alkylthio or lower alkoxy;

$R_2'$ represents hydrogen or lower alkyl;

m represents an integer from 1 to 10; $R_4$ represents hydroxy, lower alkoxy or amino; or a pharmaceutically acceptable salt thereof.

6. A compound as claimed in claim 5 wherein $R_1'$ represents hydrogen, methyl, chloro, fluoro, trifluoromethyl, hydroxy, methylthio or methoxy; $R_2'$ represents hydrogen; m represents an integer from 3 to 8; $R_4$ represents hydroxy, ethoxy, methoxy or amino; or a pharmaceutically acceptable salt thereof.

7. A compound as claimed in claim 5 wherein $R_1'$ represents hydrogen or chloro; $R_2'$ represents hydrogen; m is 4 or 5; $R_4$ represents hydroxy; or a pharmaceutically acceptable salt thereof.

8. A compound of the formula

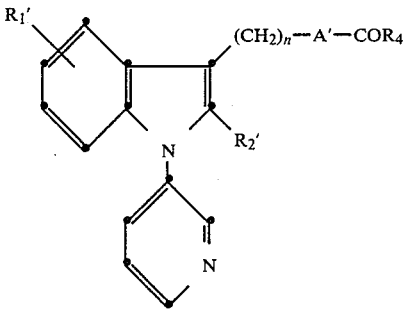

(III)

wherein $R_1'$ represents hydrogen, lower alkyl, halogen, trifluoromethyl, hydroxy, lower alkylthio or lower alkoxy; $R_2'$ represents hydrogen or lower alkyl; $R_4$ represents hydroxy, lower alkoxy or amino; n represents an integer from 1 to 4; A' represents (thio or oxy)-alkylene of 1 to 4 carbon atoms, (thio or oxy)-1,4-phenylene, 1,4-phenylene, ethenylene or lower alkyl-substituted ethenylene; or a pharmaceutically acceptable salt thereof.

9. A compound as claimed in claim 8 wherein A' is ethenylene or lower alkyl-substituted ethenylene; n represents the integer 2 or 3; or a pharmaceutically acceptable salt thereof.

10. A compound as claimed in claim 5 being 3-(4-carboxybutyl)-N-(3-pyridyl)-indole or a pharmaceutically acceptable salt thereof.

11. A compound as claimed in claim 5 being 3-(4-carboxybutyl)-5-chloro-N-(3-pyridyl)indole or a pharmaceutically acceptable salt thereof.

12. A compound as claimed in claim 8 being 3-(4-carboxypent-3-enyl)-N-(3-pyridyl)indole, a stereoisomer, or a pharmaceutically acceptable salt thereof.

13. A compound as claimed in claim 8 being 3-[3-(3-carboxymethylthio)propyl]-N-(3-pyridyl)-indole or a pharmaceutically acceptable salt thereof.

14. A pharmaceutical composition suitable for administration to mammals for the treatment of diseases responsive to inhibition of thromboxane synthetase comprising an effective amount of a compound of claim 1 in combination with one or more pharmaceutically acceptable carriers.

15. A method of selectively inhibiting the synthesis of thromboxane in a mammal comprising the administration to a mammal in need thereof of an effective amount of a compound of claim 1 in combination with one or more pharmaceutically acceptable carriers.

16. A method of treating diseases responsive to thromboxane synthetase inhibition in mammals comprising the administration to a mammal in need thereof of a therapeutically effective thromboxane synthetase inhibiting amount of a compound of claim 1 in combination with one or more pharmaceutically acceptable carriers.

17. A method of treating cardiovascular diseases in mammals comprising the administration to a mammal in need thereof of an effective thromboxane synthetase inhibiting amount of a compound of claim 1 in combination with one or more pharmaceutically acceptable carriers.

* * * * *

UNITED STATES PATENT AND TRADEMARK OFFICE
CERTIFICATE OF CORRECTION

PATENT NO. : 4,536,505

DATED : August 20, 1985

INVENTOR(S) : Leslie J. Browne

It is certified that error appears in the above-identified patent and that said Letters Patent is hereby corrected as shown below:

Column 8, structure IV should read

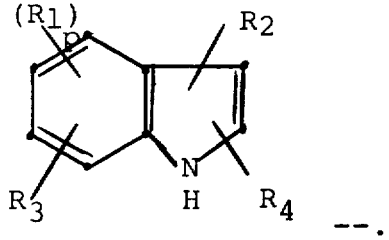

--.

[SEAL]

Signed and Sealed this

Seventeenth Day of June 1986

Attest:

DONALD J. QUIGG

Attesting Officer

Commissioner of Patents and Trademarks